United States Patent [19]
Jacob et al.

[11] Patent Number: 6,036,956
[45] Date of Patent: *Mar. 14, 2000

[54] METHOD AND DOSAGE FORM USING AN ANTAGONIST TO GAMMA INTERFERON TO CONTROL MHC-ASSOCIATED AUTOIMMUNE DISEASE

[75] Inventors: Chaim O. Jacob, Mt. View; Hugh O. McDevitt, Palo Alto, both of Calif.; Peter van der Meide, Woubrugge, Netherlands; Joseph H. Holoshitz, Palo Alto, Calif.

[73] Assignee: The Leland Stanford Junior University, Stanford, Calif.

[*] Notice: This patent issued on a continued prosecution application filed under 37 CFR 1.53(d), and is subject to the twenty year patent term provisions of 35 U.S.C. 154(a)(2).

[21] Appl. No.: 08/344,360

[22] Filed: Nov. 23, 1994

Related U.S. Application Data

[63] Continuation of application No. 07/866,114, Apr. 7, 1992, abandoned, which is a continuation of application No. 07/366,320, Jun. 14, 1989, abandoned, which is a continuation of application No. 07/087,015, Aug. 18, 1987, abandoned.

[51] Int. Cl.[7] .......................... A61K 39/395; C07K 16/24
[52] U.S. Cl. ................. 424/145.1; 424/85.4; 424/158.1; 530/388.23; 530/389.2
[58] Field of Search .............................. 424/85.4, 145.1, 424/158.1; 435/69.6, 70.21, 172.2, 172.3, 240.27, 252.3, 252.33, 320.1, 449, 452; 530/351, 388.23, 389.2

[56] References Cited

U.S. PATENT DOCUMENTS

| | | | |
|---|---|---|---|
| 4,362,155 | 12/1982 | Skurkovich | 530/351 |
| 4,514,507 | 4/1985 | Secher | 435/68 |
| 4,599,306 | 7/1986 | Altrock | 435/240.27 |
| 4,666,865 | 5/1987 | Chang et al. | 435/240.27 |
| 4,883,784 | 11/1989 | Kaneko . | |
| 4,885,290 | 12/1989 | Asano et al. . | |
| 4,897,264 | 1/1990 | Novick et al. | 435/183 |
| 4,908,387 | 3/1990 | Levine et al. . | |
| 4,920,097 | 4/1990 | Gottlieb et al. . | |
| 5,556,754 | 9/1996 | Singer et al. . | |
| 5,571,499 | 11/1996 | Hafler et al. . | |
| 5,571,500 | 11/1996 | Hafler et al. . | |
| 5,607,675 | 3/1997 | Strom . | |
| 5,695,785 | 12/1997 | Ofosu-Appiah . | |

FOREIGN PATENT DOCUMENTS

| | | |
|---|---|---|
| 1335792 | 8/1988 | Canada . |
| 0240975 | 10/1987 | European Pat. Off. . |
| 0 304 291 B1 | 1/1994 | European Pat. Off. . |
| 2646114 | 6/1989 | Japan . |

OTHER PUBLICATIONS

Acha–Orbea et al. "T Cell Receptors in Murine Autoimmune Diseases" (1989) *Ann. Rev. Immunol.* 7:371–405.
Billiau, A. "Gamma–interferon: the match that lights the fire?" (1988) *Immunol Today* 9(2):37–40.
Braude et al. "In Vitro Suppression of Anti–DNA Antibody and Immunoglobulin Syntheses in Systemic Lupus Erythematosus Patients by Human Gamma Interferon" (1988) *J. Rheumatol.* 15(3):438–444.
Cooper et al. "Suppression of Murine Collagen–induced Arthritis with Monoclonal Anti–Ia Antibodies and Augmentation with IFN–γ" (1988) *J. Immunol.* 141:1958–1962.
Dijkmans et al. "Interferon γ : a master key in the immune system" (1988) *Curr. Opin. Immunol.* 1:269–274.
Funauchi et al. "Mixed Lymphocyte Reaction in Interferon–γ Treated (NZB× NZW)$F_1$ Mice" (1989) *Toh. J. Exp. Med.* 158:155–161.
Heremans et al. "Interferon treatment of NZB Mice: Accelerated Progression of autoimmune Disease" (1978) *Infect. Immun.* 21(3):925–930.
Klippel et al. "New Therapies for the Rheumatic Diseases" (1989) *Bullet. Rheumatic. Dis* 38(4):1/8.
Mackay et al. "Premises for immune interventional therapy in rheumatoid arthritis" (1988) *Postgrad. Med. J.* 64:522–530.
Minoda et al. "Effect of Interferon–γ on the Abnormality of T Cell Activation in NZB Mice" *Clin. Immunopath.* (1988) 49:283–291.
Minoda et al. "Examination of the inhibitory effects of interferon–γ on interleukin–4–induced stimulation of resting B cells from NZB/NZW F1 mice" (1989) *Clin. Exp. Immunol.* 78:115–119.
Schattner, A. "Screeing of herpes simples virus during pregnancy" (1988) *Brit. Med. J.* 290.
Skurkovich et al. "A Disturbance of Interferon Synthesis with the Hyperpduction of Unusual Kinds of Interferon can Trigger Autoimmune Disease and Play a Pathogenetic Role in AIDS: The Removal of These Interferons can be Therapeutic" (1993) *Med. Hypoth.* 41:177–185.
Skurkovich et al. "A Disturbance of Interferon Synthesis with the Hyperpduction of Unusual Kinds of Interferon can Trigger Autoimmune Disease and Play a Pathogenetic Role in AIDS: The Removal of These Interferons can be Therapeutic" (1994) *Med. Hypoth.* 42:27–35.
Strigard, K. "Experimental allergic neuritis; studies on pathogenesis and immunoregulation" (1989) *Acta Neurol. Scand.* 123(80):7–29.
Adelman et al., "Treatment of (NZB × NZW)$F_1$ Disease with Anti–I–A Monoclonal Antibodies" *J. Exp. Med.* (1983) 158: 1350–1355.
Andrews et al., "Spontaneous Murine Lupus–Like Syndromes" *J. Exp. Med.* (1978) 148: 1198–1215.
Bessis et al., "Anti–inflammatory cytokines as treatment of inflammtion in models of autoimmune diseases" *C.R. Seances Soc. Biol. Fil.* (1995) 189: 579–590.
Boissier et al., "Biphasic effect of interferon–γ in murine collagen–induced arthritis" *Eur. J. Immunol.* (1995) 25: 1184–1190.
Knight and Adams, "Three Genes for Lupus Nephritis in NZB × NZW Mice" *J. Exp. Med.* (1978) 147: 1653–1660.

(List continued on next page.)

Primary Examiner—Robert D. Budens
Attorney, Agent, or Firm—Morrison & Foerster LLP

[57] ABSTRACT

The present invention is directed to immunotherapeutic methos for treating systemic lupus erythematosus (SLE) by administerring polyclonal or monoclonal antibodies specific for gamma interferon (IFN-gamma).

9 Claims, 3 Drawing Sheets

OTHER PUBLICATIONS

Kuby, J., "Autoimmunity" *Immunology* (1994) Chapter 19, Second Edition, W.H. Freeman and Company, New York, pp. 451–452.

Primi et al., "Genetic Control of Lymphocyte Suppression" *J. Immunology* (1978) 121: 2241–2243.

Tang et al., "The effects of a monoclonal antibody to interferon-γ on experimental autoimmune thyroiditis (EAT): prevention of disease and decrease of EAT–specific T cells" *Eur. J. Immunol.* (1993) 23: 275–278.

Theofilopoulos et al., "Murine Models of Systemic Lupus Erythematosus" *Adv. Immun.* (1985) 37: 269–390.

Abbas et al., *Cellular and Molecular Immunology*, Wonsiewicz, ed. (1991), pp. 319–331 and pp. 354–376.

McEvoy and Thomas (1990) in *Autoimmunity and the Pathogenesis of Diabetes* (Ginsberg–Fellner and McEvoy eds.) Springer–Verlag, New York, pp. 165–183.

Oi, V.T. et al., "Immunoglobulin gene expression in transformed lymphoid cells" *Proc. Natl. Acad. Sci. USA* (1983) 80:825–829.

Campbell et al., "IFN-γ Induces Islet Cell MHC Antigens and Enhances Autoimmune, Streptozotocin–Induced Diabetes in the Mouse", *J. Immunol.*, 140:1111–1116 (1988).

Debray–Sachs et al., "Prevention of Diabetes in NOD Mice Treated with Antibody to Murine IFNγ", *J. Autoimm.*, 4:237–248 (1991).

Watanabe and Jacob, "Regulation of MHC Class II Antigen Expression", *J. Immunol.*, 146:899–905 (1991).

Jacob et al., "Monoclonal Anti–Tumor Necrosis Factor Antibody Renders Non–Obese Diabetic Mice Hypersensitive to Irradiation and Enhances Insulitis Development", *Intl. Immunol.*, 4:611–614 (1992).

Jacob and McDevitt, *Interferon-γ and TNF Autoimmune Disease Models*, pp. 107–126 (1991).

Isaacs et al., "Humanised monoclonal antibody therapy for rheumatoid arthritis" *The Lancet* (1992) 340:748–752.

Bacha et al., "Anti–arthritic effects demonstrated by an interleukin–2 receptor–targeted cytotoxin ($DAB_{486}IL-2$) in rat adjuvant arthritis" *Eur. J. Immunol.* (1992) 22:1673–1679.

News Release Summary dated May 3, 1993, Seragen, Inc..

Smith et al., (1983) Ann. Rev. Immunol. 1:175–210.

McDevitt, (1986) Clinical Research 34(2):163–175.

Bottazzo et al., (1983) Lancet, p. 1115–1119.

Hooks et al., (1980) Annals New York Academy of Sciences, p. 21–32.

Hooks et al., (1979) New England Journal of Medicine 301(1):5–8.

Iwatani et al., (1986) Journal of Clinical Endocrinology and Metabolism 63(3):695–708.

Marx, (1988) Science 242:863–865.

Lafferty et al., (1983) Ann. Rev. Immunol. 1:143–173.

Mason et al., (1986) Ann. Rev. Immunol. 4:119–145.

Regulation of Immune Gene Expression, Edited by Marc Feldman and Andrew McMichael (Humana Press, NJ), p. 258–271.

Dijkema et al, (1985) EMBO Journal 4:761–767.

Van Der Meide et al., (1986) J. Gen. Virol. 67:1059–1071.

Schwartz, R.S., "Autoimmunity and Autoimmune Diseases," in *Fundamental Immunology*, $3^{rd}$ Ed., Paul, W.E., Ed., Raven Press, Ltd., New York, 1993, pp. 1033, 1069–1074.

Brostoff et al., "SLE and Other Connective Tissue Disorders," in *Clinical Immunology*, Brostoff et al., Eds., Gower Medical Publishing, New York, 1991, p. 6.1–6.14.

Patterman et al, "Murine Models of Spontaneous Systemic Lupus Erythematosus," in *Autoimmune Disease Models: A Guidebook*, Cohen et al., Eds., Academic Press, San Diego, 1994, p. 217–243.

Nicoletti et al., "In Vivo Treatment With A Monoclonal Antibody to Interferon Gamma Neither Affects The Survival Nor The Incidence of Lupus–Nephritis In The MRL/pr–/pr Mouse," *Immunopharmacology* 24:11–16, 1992.

Jacob et al., "In Vivo Treatment of (NZB × NZW)F1 Lupuslike Nephritis With Monoclonal Antibody to γ Interferon," *J. Exp. Med.* 166:798–803, Sep. 1987.

Golbus et al., "Increased Immunoglobulin Response to γ–Interferon By Lymphocytes From Patients With Systemic Lupus Erythematosus," *Clin. Immunology Immunopath.* 46:129–140, 1988.

Braude et al., "In Vitro Suppression Of Anti–DNA Antibody and Immunoglobulin Synthesis In Systemic Lupus Erythematosus Patients By Human Gamma Interferon," *J. Rheumatol.* 15(3):438–444, Mar. 1988.

Jacob et al., "Tumor Necrosis Factor Alpha In Murine Systemic Lupus Erythematosus Disease Models: Implications For Genetic Predisposition And Immune Regulation," *Cytokine* 3(6):551–561, Nov. 1991.

Ozmen et al., "Experimental Therapy of Systemic Lupus Erythematosus: The Treatment of NZB/w Mice With Soluble Interferon–γ Receptor Inhibits The Onset of Glomeralo nephritis," *Eur. J. Immunol.* 25:6–12, 1995.

Ozmen et al., "Soluble Interferon–γ Receptor: A Therapeutically Useful Drug For Systemic Lupus Erythematosus," *J. Interferon Res.* 14:283–284, 1994.

Horwitz et al., "The Cytokine Network In The Pathogenesis Of Systemic Lupus Erythematosus And Possible Therapeutic Implications," *Springer Semin Immunopathol.* 16:181–200, 1994.

Landolfo et al, *Science*, 229 176–9, (1985).

Raghavacher et al, *Biol Abs*, 82(10);96111, (Nov. 15, 1986).

Pujol–Borrell et al, *Biol Abs*, 82(9);83178 (Nov. 1, 1986).

Engleman et al, *Biol Abs*, 573(7);4845 (1982).

Bocci et al, *Biol Abs.*, 81(5);43023, (Mar. 1, 1986).

Larrick et al, *J. Biol. Resp. Mod.*, 5:, 379–93, (1986).

McClelland et al, Clinics in Haemotology, 13(1), 39–72, (Feb. 1984).

Hanbook of Exp. Immunol., vol. 2, "Cellular Immunology," (Weir, Editor), Blackwell Sci, Pub. (1986).

Benacerraf, in Weir above, p 72.1–72.4.

White et al, in Weir, above, p 81.1–81.2.

Waldmann, T.A., "Monoclonal Antibodies in Diagnosis and Therapy," *Science* 252:1657–1662, Jun. 21, 1991.

METHOD AND DOSAGE FORM USING AN ANTAGONIST TO GAMMA INTERFERON TO CONTROL MHC-ASSOCIATED AUTOIMMUNE DISEASE

This application is a continuation of application Ser. No. 07/866,114, filed Apr. 7, 1992, now abandoned, which is a continuation of application Ser. No. 07/366,320, filed Jun. 14, 1989, now abandoned, which is a continuation of application Ser. No. 07/087,015, filed Aug. 18, 1987, now abandoned. gamma interferon (IFN-gamma).

REFERENCE TO GOVERNMENT GRANT

The United States Government has rights to Lhis invention pursuant to Grant Nos. AI-11313 and AI 07757, awarded by the National Instititutes of Health.

DESCRIPTION

1. Technical Field

The invention is in the field of immunotherapy. More specifically, it relates to controlling autoimmune diseases associated with particular regions of the major histocompatibility complex (MHC), such as those encoding the Class II antigens, by suppressing the immune response(s) controlled by the region with an antagonist to interferon gamma (IFN-$\gamma$).

2. Background Art

Autoimmune diseases are the result of an immune response directed against a self antigen. Although the primary causes of these diseases are unknown, many of the diseases are associated with serologically defined alleles of the Human Leukocyte Antigen (HLA) complex, more specifically the alleles which encode the Class II antigenic molecules. The primary role of the Class II molecules, which include the HLA-D and HLA-DR antigens in humans and the Ia antigens in rodents, appears to mediate communication between immunocompetent cells. Thus, the induction of activated T helper lymphocytes requires presentation of specific antigens by MHC class II antigen-positive cells.

Induction of class II antigens seems to be relevant to certain pathologic states. Thus, epithelial cells which are normally HLA-class II negative, express these molecules in patients with several autoimmune diseases, such as Graves' disease, Hashimoto's thyroiditis, insulin dependent diabetes mellitus and primary biliary cirrhosis.

Interferon gamma (IFN-$\gamma$) leads to enhancement of synthesis and surface expression of MHC class II antigens in a wide variety of cell types, both in mice and humans. Induction of these MHC antigens by IFN-$\gamma$ may occur in several cell types that otherwise express low or undetectable levels of Ia molecules. Acquisition of antigen-presenting capacity after in vitro induction of Ia expression has been demonstrated for murine macrophages, rat astrocytes, human vascular endothelial cells and dermal fibroblasts. However, other lymphokines and cellular factors in addition to IFN-$\gamma$, such as interferon-$\alpha$ and interferon-$\beta$ as well as interleukin-4 (BSF-1), have also been shown to stimulate class II MHC expression.

Possible methods of treating or preventing the expression of autoimmune diseases involve immunosuppression. Immunosuppression is commonly achieved through treatment with a means and/or agent such as radiation, antimitotics, heterologous antilymphocyte sera, heterologous anti-T cell antibodies, adrenal steroids, and cytotoxic chemicals. These treatments are nonspecific in the sense that they suppress the entire immune system rather than a single immune response. A major side effect of nonspecific immunosuppression is immunodeficiency, which leaves the treated individual highly susceptible to bacterial, viral, and fungal infections that would otherwise be manageable, but are under the circumstances life-threatening.

Antibodies are the most inherently specific natural immunosuppressive agents. Antibody regulation of the mouse immune system has been reported by Greene et al. (1977), Proc. Natl. Acad. Sci. U.S.A. 74, 5118 and Meruelo et al. (1980), Proc. Natl. Acad. Sci. U.S.A. 77, 2178. Their experiments indicated that different anti-Ia sera could both increase and decrease tumor growth in vivo. This correlated with suppression or enhancement of the specific immune response. In vivo administration of monoclonal antibodies specific for an Ia region gene product induced remission in NZB/W $F_1$ mice with moderate renal disease. Adelman et al. (1983), J. Exp. Med. 158, 1350. These mice are a model for systemic lupus erythematosus. Anti-Ia monoclonal antibodies have also been given to animals in several other autoimmune disease models. This treatment was effective in experimental allergic encephalitis (a model for the human disease, multiple sclerosis)(Steinman et al. (1981), Proc. Natl. Acad. Sci. U.S.A. 78, 711), in experimentally induced myasthenia gravis (Waldor et al.(1983), Proc. Natl. Acad. Sci. U.S.A. 80, 2713), and in spontaneous autoimmune diabetes and thyroiditis in BB/W rats (Boitard et al. (1985), Proc. Natl. Acad. Sci. U.S.A. 82, 6627).

Antibody immunosuppressive therapy is used in certain instances in humans, such as for preventing Rh-related erythroblastosis fetalis. This mode of treatment, however, is limited to diseases in which the offending antigen is known, and a specific human antiserum is available.

The prime objective of the present invention is to provide a technique for treating genetically controlled, MHC associated autoimmune diseases via selective immunosuppression.

DISCLOSURE OF THE INVENTION

The invention is based upon the discovery that treatment with an antagonist to IFN-$\gamma$, more specifically, an antibody directed against IFN-$\gamma$, delayed and alleviated the symptoms of an MHC-linked autoimmune disease in mammals. Accordingly, one aspect of the invention is an immunotherapeutic method for treatment of an individual to control a disease associated with an MHC-linked immune response gene of the individual. The method comprises administering a disease-controlling amount of an antagonist of IFN-$\gamma$ to the individual.

Another aspect of the invention is an immunotherapeutic method for treatment of an individual to control a disease associated with an MHC-linked immune response gene of the individual. The method comprises administering a disease-controlling amount of antibodies directed against IFN-$\gamma$ to the individual.

Still another aspect of the invention is a unit dosage form for treatment of the above-described individuals. The unit dosage form is comprised of antibodies against IFN-$\gamma$ combined with a pharmaceutically acceptable vehicle. The amount of antibodies in the dosage form is sufficient to substantially lessen manifestation of the disease. Manifestation of the disease may be determined by clinical symptoms associated with the disease, and/or by the presence of antibodies directed against a self-product, said antibodies being associated with the disease, and being absent in healthy individuals.

Yet another aspect of the invention is an immunotherapeutic method for the treatment of the above described individuals which comprises administering a disease-controlling amount of antibodies directed against a cellular receptor for IFN-γ to the individual.

MODES FOR CARRYING OUT THE INVENTION

Figure 1:
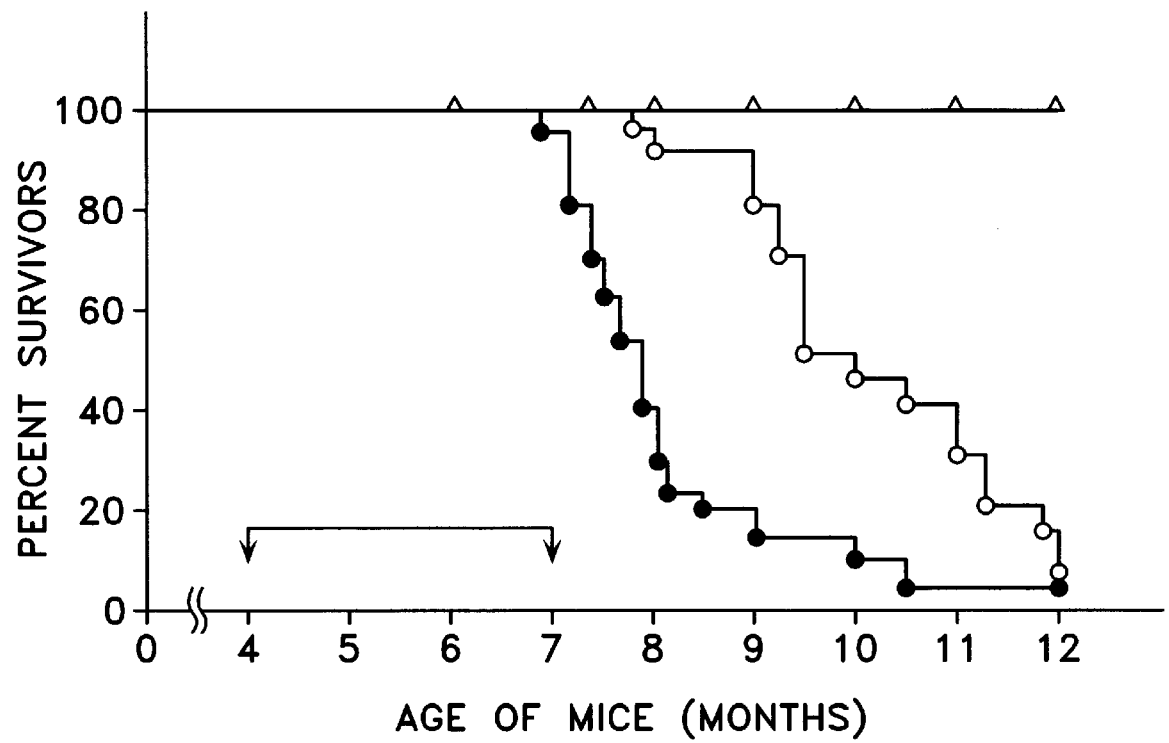
FIG. 1 presents a graph showing the survival of NZB/W $F_1$ female mice treated with IFN-γ.

The practice of the present invention will employ, unless otherwise indicated, conventional techniques of molecular biology, microbiology, recombinant DNA, and immunology, which are within the skill of the art. Such techniques are explained fully in the literature. See, e.g., Maniatis, Fritsch and Sambrook, MOLECULAR CLONING: A LABORATORY MANUAL (1982); DNA CLONING, Volumes I and II (D.N. Glover ed. 1985); OLIGONUCLEOTIDE SYNTHESIS (M.J. Gait ed. 1984); NUCLEIC ACID HYBRIDIZATION (B. D. Hames and S. J. Higgins, eds. 1984); TRANSCRIPTION AND TRANSLATION (B. D. Hames and S. J. Higgins, eds 1984): ANIMAL CELL CULTURE (R. K. Freshney, ed. 1986); IMMOBILIZED CELLS AND ENZYMES (IRL press, 1986); B. Perbal, A PRACTICAL GUIDE TO MOLECULAR CLONING (1984); the series, METHODS IN ENZYMOLOGY (S. Colowick and N. Kaplan, eds., Academic Press, Inc.), and HANDBOOK OF EXPERIMENTAL IMMUNOLOGY, Volumes I–IV (D. M. Weir and C. C. Blackwell, eds., 1986, Blackwell Scientific Publications).

In describing the present invention, the following terminology will be used in accordance with the definitions set out below.

The "Major Histocompatibility Complex" (MHC) denotes a region of the genome which encodes proteins involved in immunological recognition. The MHC complex in humans is termed the "HLA" complex, and in mice is termed the H-2 complex.

"Class II antigens or molecules" refer to those encoded within the HLA-D or HLA-DR locus in humans, within the I region in mice, and comparable regions in other species.

"Gamma interferon (IFN-γ)" refers to that interferon polypeptide which is produced by T lymphocytes upon induction with mitogens, or upon antigenic stimulation of sensitized cells; it refers to the polypeptide in its varied glycosylated forms, as well as to the unglycosylated polypeptide, all of which may be synthesized naturally, or by recombinant techniques.

"Antagonist to IFN-γ" refers to an agent which interferes with the physiological activity of IFN-γ by any mechanism, including, for example, preventing the binding of IFN-γ to a cellular receptor, preventing the synthesis of an IFN-γ cellular receptor, or preventing the synthesis of IFN-γ. Antagonists to IFN-γ include antibodies to IFN-γ and to the cellular receptor(s) for IFN-γ activity, and drugs which inhibit IFN-γ activity. A peptide may be part of the IFN-γ polypeptide sequence, part of the receptor sequence or a mimitope.

"Mimitope" is a peptide which has the spatial structure of a biologically important site, e.g., an epitope, or an enzyme active site, or a receptor binding site.

"Peptide" refers to a polyamino acid chain wherein the amino acids are linked by peptide bonds. Peptide does not connote size, and for the purposes herein is used interchangeably with oligopeptide and polypeptide. In addition, peptide does not define the structural modifications, including glycosylation. Hence, a polypeptide may or may not be glycosylated.

"Antibody" refers to a member of a family of glycosylated proteins called immunoglobulins, which can specifically combine with an antigen "Antigen" refers to a protein or peptide compound which will produce antibody formation without chemical modification.

"Epitope" refers to the actual site of antibody recognition of the antigen. The term is also used interchangeably with "antigenic determinant" or "antigenic determinant site".

"Carrier" is a material to which the antigen is bound or conjugated, and which presents it as a recognizable immunogen to the immune system.

"Conjugate" refers to an antigen or hapten chemically bonded to a carrier; a conjugate can contain other groups, as well.

The term "control" and conjugates thereof that are used herein to describe the purpose and/or result of the treatment are intended to mean prophylaxis and/or therapy. Accordingly the invention may be used to prevent or alleviate a disease associated with a particular immune response allele of the MHC of the individual being treated.

It is known that all mammals and probably all vertebrates possess basically equivalent MHC systems, and that immune response genes are linked to the MHC. The invention may, therefore, be used to treat autoimmune diseases in vertebrate animals, particularly in mammals. It is expected that the immunotherapeutic method of the invention will be used primarily in humans, as well as in domestic, pet, and sport animals.

Associations between the human MHC, denoted HLA and susceptibility to diseases are reported in the HLA and disease Registry which is kept and published in Copenhagen by Ryder and Svejgaard. Such associations are determined by comparing the HLA types of a diseased population with the HLA types of a healthy population. Many diseases are associated with more than one HLA specificity. Most associations have involved the D region of the HLA. Some are race specific. The association of a particular HLA allele with susceptibility to a disease is usually dominant. The following Tables present a list of diseases which are known to be associated with specific HLA antigens (Table 1), and the antigen(s) showing the strongest association with a particular disease (Table 2). See Thomson in Handbook of Experimental Immunology, volume 3: Genetics and Immunology (Herzenberg, Blackwell, and Herzenberg eds. 1986, Blackwell Scientific Publications, pp. 102.1–102.12).

TABLE 1

Diseases Known to be Associated with Specific RLA Antigens

Rheumatology

Ankylosing spondylitis
Reiter's disease
Yersinia arthritis
Salmonella arthritis
Shigella arthritis
Psoriatic arthritis
Juvenile rheumatoid arthritis
Acute anterior uveitis
Rheumatoid arthritis Rheumatic heart disease

Neurology

Multiple sclerosis
Optic neuritis
Myasthenia gravis
Paralytic poliomyelitis

Dermatology

Psoriasis vulgaris

Dermatitis herpetiformis
Pemphigus vulgaris
Behcet's disease
Recurrent herpes labialis
Alopeica areata

Allergology

Dust allergy

Rye grass group I allergy
Avian hypersensitivity
Hay fever
Ragweed allergy
Grass pollinosis

Endocrinology

Juvenile insulin-dependent diabetes
Thyrotoxicoses (Graves' disease)
Hashimoto's thyroiditis
de Quervain's thyroiditis
Congential adrenal hyperplasia
Idiopathic Addison's disease

Gastroenterology

Coeliac disease
Pernicious anaemia

Atrophic gastritis
Autoimmune chronic active hepatitis
Hepatitis B associated chronic active hepatitis

Immunopathology

Systemic lupus erythematosus
Sicca syndrome
Goodpasture's syndrome
IgA nephropathy
$C_2$ deficiency

Malignant diseases

Retinoblastoma
Rodgkin's disease
Acute lymphatic leukemia
Nasopharyngeal carcinoma

TABLE 2

Antigen Association Data for Some of the HLA-Associated Diseases

| Disease | HLA | Patients | Controls | Relative risk | Attributable risk ($\delta$) |
|---|---|---|---|---|---|
| Hodgkin's disease | A1 | 40 | 32.0 | 1.4 | 0.12 |
| Idiopathic haemochromatosis | A3 | 76 | 28.2 | 8.2 | 6.67 |
| Behcet's disease | B5 | 41 | 10.1 | 6.3 | 0.34 |
| Congenital adrenal hyperplasia | B47 | 9 | 0.6 | 15.4 | 0.08 |
| Ankylosing spondylitis | B27 | 90 | 9.4 | 87.4 | 0.89 |
| Reiter's disease | B27 | 79 | 9.4 | 37.0 | 0.77 |
| Acute anterior uveitis | B27 | 52 | 9.4 | 10.4 | 0.47 |
| Subacute thyroiditis | B35 | 70 | 14.6 | 13.7 | 0.65 |
| Psoriasis vulgaris | Cw6 | 87 | 33.1 | 13.3 | 0.81 |
| Dermatitis herpetiformis | D/DR3 | 85 | 26.3 | 10.8 | 0.72 |
| Coeliac disease | D/DR3 | 79 | 26.3 | 15.4 | 0.80 |
| Sicca syndrome | D/DR3 | 78 | 26.3 | 9.7 | 0.70 |
| Idiopathic Addison's disease | D/DR3 | 69 | 26.3 | 6.3 | 0.58 |
| Graves disease | D/DR3 | 56 | 26.3 | 3.7 | 0.42 |
| Insulin-dependent diabetes | D/DR3 | 56 | 28.2 | 3.3 | 0.39 |
|  | D/DR4 | 75 | 32.2 | 6.4 | 0.63 |
|  | D/DR2 | 10 | 30.S | 0.2 | — |
| SLE | D/DR3 | 70 | 28.2 | 5.8 | 0.58 |
| Multiple sclerosis | D/DR2 | 59 | 25.8 | 4.1 | 0.45 |
| Optic neuritis | D/DR2 | 46 | 25.8 | 2.4 | 0.27 |
| Rheumatoid arthritis | D/DR4 | 50 | 19.4 | 4.2 | 0.38 |
| IgA nephropathy | D/DR4 | 49 | 19.5 | 4.0 | 0.37 |
| Hydralazine-induced SLE | D/DR4 | 73 | 32.7 | 5.6 | 0.60 |
| Hashimoto's thyroiditis | D/DRS | 19 | 6.9 | 3.2 | 0.13 |
| Pernicious anaemia | D/DR5 | 25 | 5.8 | 5.4 | 0.20 |
| Pauciarticular onset juvenile rheumatoid arthritis | D/DR5 | 50 | 16.2 | 5.2 | 0.40 |

It has been hypothesized that the inappropriate expression of MHC class II molecules by epithelial or other cells might enable these cells to present their own surface molecules to autoreactive T cells, and thus make an important contribution to the initiation and potentiation of the autoimmune process. Bottazzo et al. (1983), Lancet 2, 1115. In addition, it seems possible that the induction of Ia antigens is due to release of IFN-γ by activated T cells. Moreover, it has been found that rat astrocytes induced in vitro to express Ia by IFN-γ were able to present myelin basic protein to encephalitogenic T cell lines in an MHC-restricted manner. Fontana et al. (1984), Nature (London) 307, 273. Thus, IFN-γ may play a role in up-regulating the autoimmune process, and blocking the effect of IFN-γ may down-regulate this process.

According to the invention, autoimmune diseases associated with the regions of the HLA locus encoding class II molecules are controlled by selective immunosuppression using antagonists of IFN-γ which prevent the physiological response(s) induced by IFN-γ, more specifically, those responses which are involved in the up-regulation of the autoimmune process. Antagonists of IFN-γ include, for example, drugs and peptides which suppress the synthesis of IFN-γ, such as neuropeptide hormones or peptides which are immunoreactive with neuropeptide hormones. The regulation of IFN-γ by ACTH and a peptide which is immunoreactive with ACTH has been discussed by Johnson et al (1984), J. Immunol. 132, 246.

Antagonists of IFN-γ also include molecules, for example, peptides, which prevent or inhibit the interaction of IFN-γ with a cellular receptor involved in the up-regulation of the autoimmune response. Examples of this type of antagonist include peptides which mimic the tertiary conformation of IFN-γ and thereby are either competitive, noncompetitive, or uncompetitive inhibitors of IFN-γ with respect to receptor binding. Also included are antibodies to IFN-γ, and antibodies to the IFN-γ cellular receptor. These antibodies may be polyclonal or, preferably, monoclonal. In addition, they may be chimeric molecules incorporating light and heavy chain regions from different species, and which are expressed from recombinant DNAs. See, for example, Tan et al (1985), J. Immunol. 135, 3564. An example of this type of antibody could be one in which the hypervariable regions from non-human antibodies are inserted into the human $V_H$ or $V_L$ framework sequences.

Antibodies directed against IFN-γ may be made by any of the known techniques, using IFN-γ, or immunogenic peptides of IFN-γ, as the immunogen. IFN-γ used as the immunogen may be synthesized naturally, e.g., by induction of peripheral blood lymphocytes by phytohemaglutinin and phorbol myristic acetate, and purified. A procedure for the induction of human IFN-γ and its purification have been described by Yip et al. (1982), Science 215, 411. Alternatively, IFN-γ or its immunogenic peptides may be synthesized by recombinant techniques. Recombinant IFN-γ is available. See, e.g., Zlotnik et al. (1983), J. Immunol. 131, 2814. Immunogenic peptides of IFN-γ also may be chemically synthesized. In instances wherein the synthesized peptide is correctly configured so as to provide the correct epitope, but too small to be immunogenic, the peptide may be linked to a suitable carrier to form a conjugate.

A number of techniques for obtaining such linkages are known in the art, including the formation of disulfide linkages using N-succinimidyl-3-(2-pyridylthio) propionate (SPDP) and succinimidyl 4-(N-maleimidomethyl) cyclohexane-1-carboxylate (SMCC). (If the peptide lacks a sulfhydryl, this can be provided by addition of a cysteine residue.) These reagents create a disulfide linkage between themselves and peptide cysteine residues on one protein and an amide linkage through the ε-amino on a lysine, or other free amino group in the other. A variety of such disulfide/amide-forming agents are known. See, for example, Immun. Rev. (1982) 62, 185. Other bifunctional coupling agents form a thioether rather than a disulfide linkage. Many of these thioether-forming agents are commercially available and include reactive esters of 6-maleimidocaproic acid, 2-bromacetic acid, 2-iodoacetic acid, 4-(n-maleimidomethyl)cyclohexane-carboxylic acid, and the like. The carboxyl groups can be activated by combining them with succinimide or 1-hydroxy-2-nitro-4-sulfonic acid, sodium salt. The foregoing list is not meant to be exhaustive, and modifications of the named compounds can clearly be used.

Any carrier may be used which does not itself induce the production of antibodies harmful to the host, such as the various serum albumins, tetanus toxoids, or keyhole limpet hemocyanin (KLH).

If polyclonal antibodies are desired, a selected mammal, (e.g., mouse, rabbit, goat, horse, etc.) is immunized with IFN-γ or its immunogenic peptide or conjugate. Serum from the immunized animal is collected and treated according to known procedures. If serum containing polyclonal antibodies to IFN-γ contains antibodies to other antigens, the IFN-γ can be purified by immunoaffinity chromatography, using known procedures.

The general methodology for making monoclonal antibodies by hybridomas is well known. Monoclonal antibodies directed against IFN-γ may be made from antibody expressing hybridomas by such procedures as those described by Kohler and Milstein (1975), Nature 356, 497, Levy and Dilley (1978), Proc. Natl. Acad. Sci. U.S.A. 75. 4211; and Ollson and Kaplan, Proc. Natl. Acad. Sci., U.S.A. 77, 5429–5431. Briefly, these processes involve fusing myeloma cells and lymphocytes with a fusogen, typically polyethylene glycol. The fused cells or hybridomas are then expanded in a nutrient medium such as HAT medium. The cells surviving the incubation are assayed for production of the desired antibody and positive cells are sorted and cloned by known techniques. The monoclonal antibodies expressed by the clones may be harvested and purified by known techniques. Myeloma cell lines that may be used in the process are known and available. The lymphocytes, typically either spleen cells or B cells, are obtained from individuals immunized with IFN-γ. and which have a high titer of the desired anti-IFN-γ antibody.

Although xenogeneic antibodies may be used in the invention, it is preferable to use allogenic antibodies to reduce the likelihood of the antibodies themselves inducing an immune response from the host. An allogenic monoclonal antibody is one that is expressed by a hybridoma made by fusing cells from the same animal species as the host. The antibodies may be from one or more immunoglobulin classes (IgM, IgG, IgA, IgD, or IgE) depending upon the particular disease and individual involved. Antigen binding fragments (F(ab')$_2$, Fab, Fab', Fv) of IgG monoclonal antibodies may also be used in appropriate situations, for instance, where it is desired to reduce the likelihood of complement fixation. As used herein, the term "monoclonal antibody" is intended to include such fragments as well as whole immunoglobulins.

The anti-IFN-γ antibodies are preferably administered to the individuals in a manner that will maximize the likelihood of the antibody reaching the IFN-γ, binding to it, and thereby blocking its effect on stimulating the inappropriate expression of MHC Class II molecules that appears to underlie autoimmune diseases. Being proteins, the antibodies will normally be administered parenterally, preferably intravenously. Since they may react with white blood cells, they will preferably be administered slowly, either from a conventional IV administration set or from a subcutaneous depot. In a mouse model for systemic lupus erythematosus, a dose of anti-IFN-γ antibody of 2 mg/mouse/week for three months was sufficient to delay the expression of the disease. (See the Examples section.) The dose for individuals of different species and for different autoimmune diseases is determined by measuring the effect of the anti-IFN-γ antibody on the lessening of those parameters which are indicative of the autoimmune disease being treated. The dose of anti-IFN-γ may have to be repeated periodically depending upon the particular disease. Moreover, since the effects of many autoimmune diseases are considered irreversible, e.g., destruction of the insulin-producing islets of the pancreas during insulin dependent diabetes mellitus (IDDM), treatment of the susceptible individual will be prior to full manifestation of the disease, and possibly prior to the onset of the disease. Whether or not a disease is fully manifested may be determined by monitoring clinical symptoms, as well as the presence of specific antibodies associated with the autoimmune disease. A method for diagnosing individuals who are susceptible to an autoimmune disease prior to onset of the disease is presented in a commonly owned copending U.S. patent application, Ser. No. 036,372, filed Apr. 9, 1987, which is hereby incorporated by reference herein. When used as prophylaxis it may be possible to administer short courses of antibody or antibodies semiannually or annually. In treating an existing disease it is expected that the antibody or antibodies will be administered more frequently as needed. For autoimmune diseases that are known to be triggered or aggravated by particular environmental factors which increase the level of IFN-γ, the dosage regimen will be scheduled accordingly.

When administered parenterally the antibodies will be formulated in a unit dosage injectable form (solution, suspension, emulsion) in association with a pharmaceutically acceptable parenteral vehicle. Such vehicles are inherently nontoxic and nontherapeutic. Examples of such vehicles are normal saline, Ringer's solution, dextrose solution, and Hanks' solution. Nonaqueous vehicles such as fixed oils and ethyl oleate may also be used. A preferred vehicle is 5% dextrose/saline. The vehicle may contain minor amounts of additives such as substances that enhance isotonicity and chemical stability, e.g., buffers and preservatives. The antibody is preferably formulated in purified form substantially free of aggregates and other proteins at concentrations of about 5 to 30 mg/ml, preferably 10 to 20 mg/ml.

The following examples further illustrate the invention. These examples are not intended to limit the scope of the invention. In light of the present disclosure, numerous embodiments within the scope of the claims will be apparent to those of ordinary skill in the art.

EXAMPLES

I. Treatment of NZB/W $F_1$ Mice with IFN-γ or with Anti-IFN-γ Monoclonal Antibodies: A Model for Systemic Lupus Erythematosus in Humans The $F_1$ hybrids of autoimmune New Zealand Black (NZB) mice and the phenotypically normal New Zealand White (NZW) mouse strain develop severe systemic autoimmune disease, more fulminant than that found in the parental NZB strain. These mice manifest several immune abnormalities, including antibodies to nuclear antigens and subsequent development of a fatal, immune complex-mediated glomerulonephritis with female predominance, remarkably similar to systemic lupus erythematosus (SLE) in humans. Knight and Adams (1978), J. Exp. Med. 147, 1653.

In both the human and murine forms of the disease, a strong association with MHC gene products has been reported. HLA DR2 and HLA DR3 individuals are at a higher risk than the general population to develop SLE (Reinertsen et al. (1978), N. Engl. J. Med. 299, 515), while in NZB/W $F_1$ mice (H-$2^{u}$), a gene linked to the h-$2^u$ haplotype derived from the NZW parent contributes to the development of the lupus-like nephritis.

I.A. Treatment with IFN-γ: Effect on the Survival of NZB/W $F_1$ Mice

I.A.1. Treatment of Four Month Old Mice with IFN-γ

Two groups of 25 female NZB/W $F_1$ mice, four months of age, received recombinant IFN-γ or equivalent volumes of phosphate-buffered saline (PBS) over a period of three months. The mice were four months of age at the beginning of treatment. As an additional control group, 16 age- and sex-matched mice of the parental strain NZW were similarly treated with IFN-γ.

Murine IFN-γ manufactured in *E. coli* by recombinant technology according to the procedure of Gray and Goeddel was kindly provided by Dr. Michael Shepard, Genentech, Inc. The procedure of Gray and Goeddel (1983) for the production of IFN-γ using recombinant techniques is found in Proc. Natl. Acad. Sci. U.S.A. 80, 5842, and is hereby incorporated by reference herein. Each mouse was given interperitoneal injections of 5×10 units of IFN-γ or PBS 3 times weekly for three months.

FIG. 1 presents a graph showing the survival of NZB/W $F_1$ mice treated with IFN-γ. The closed circles represent NZB/W $F_1$ mice treated with IFN-γ; the open circles represent the age- and sex-matched NZB/W $F_1$ mice treated with PBS; and the open triangles represent the NZW parental strain treated with IFN-γ. The arrows indicate the time period of the treatment.

As seen in FIG. 1, death occurred at an earlier age in the group of NZB/W $F_1$ mice that received IFN-γ compared to the PBS control mice. The difference in survival between treated and control mice was statistically significant (p 0.001). In the IFN-γ-treated group, 75–80% of NZB/W $F_1$ mice were dead by 8 months. In contrast, in the PBS control NZB/W $F_1$ group, the mice had only begun to die at 8 months, and at 9.5 months 50% of this group of mice were still surviving. The lifespan of the NZW control group was not affected by the IFN-γ treatment.

I.A.2. Treatment of Mice of Different Ages with IFN-γ

The treatment protocol was as in I.A.1., except that treatment with IFN-γ was initiated at different ages, ranging between 2½ to 6 months. This treatment accelerated mortality when compared to age-matched control groups. When IFN-γ treatment started at 6½ months, using the same protocol. no significant difference in lifespan was observed between the group treated with IFN-γ and controls.

I.B. Treatment with Anti-IFN-γ Monoclonal Antibodies

Groups of age matched female mice were treated intraperitoneally with monoclonal anti-IFN-γ either at 2 mg×3 per week, or at 2 mg once per week; control groups of age-matched female mice were treated intraperitoneally with PBS, or with nonrelevant monoclonal antibody. All mice were four months old at the beginning of treatment.

DB-1 monoclonal anti-IFN-γ antibodies (DB-1) were purified from ascites fluid of Balb/c mice injected with $10^7$ DB-1 hybridoma cells. DB-1 cells were obtained from the TNO Primate Center, the Netherlands. Antibodies were purified by 40% ammonium sulfate precipitation (twice) followed by chromatography on a DEAE-Sephacel column.

The ability of DB-1 to inhibit IFN-γ-induced Ia expression was assayed in vitro on the murine myelomonocytic cell line WEHI-3. Treatment of these cells with murine IFN-γ for 24–48 hours induces the expression of Ia antigens on their surface. King and Jones (1983), J. Immunol. 131, 315. Treatment of WEHI-3 cells with 10 U/ml of murine IFN-γ in the presence of DB-1 at 0.5 mg/ml caused inhibition of about 70% of Ia expression as detected with fluorescein-conjugated MK-D6 (anti-Ia$^d$) monoclonal antibody on a fluorescence-activated cell sorter (FACS IV).

I.B.1. Effect on the Survival of NZB/W $F_1$ Mice

Figure 2:
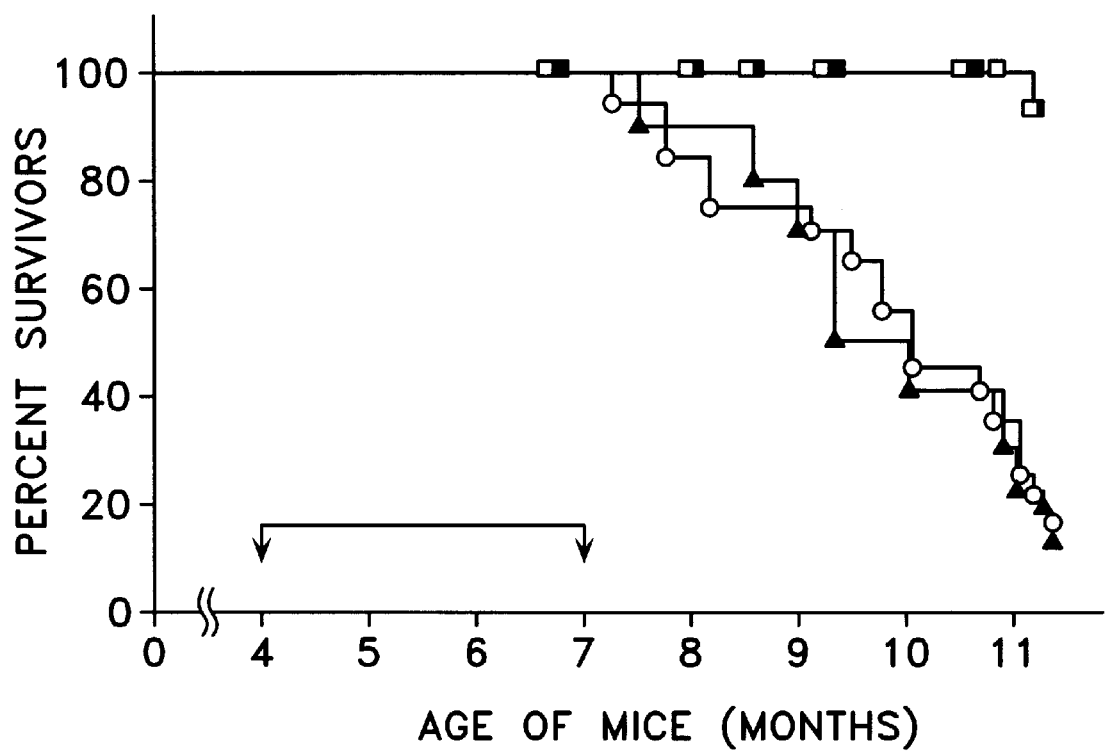
FIG. 2 presents a graph showing the prolonged survival of NZE/W $F_1$ mice treated with anti-IFN-γ monoclonal antibodies.

FIG. 2 shows the improved survival rate of mice treated with DB-1. The closed triangles indicate mice treated with PBS; the open circles indicate mice treated with the non-relevant monoclonal antibody; the closed squares indicate mice treated with DB-1 at 2 mg×3 per week; and the open squares indicate mice treated with DB-1 at 2 mg once per week.

As shown in FIG. 2, at the age of 11 months, 80–85% of the mice in both control groups were dead. In contrast, 95% of the mice in both DB-1-treated groups were alive at this time. There was no difference found between mice given weekly 2 mg injections of DB-1 compared to those receiving 2 mg antibody 3 times per week.

I.B.2. Effect on the Development of Significant Proteinuria

Proteinuria was measured colorimetrically by the use of Uristix (Miles Laboratories, Inc., Elkhart, Ind.). This produces an approximation of proteinuria as follows: trace, 10 mg/dl; 1+, 30 mg/dl; 2+, 100mg/dl; 3+, 300 mg/dl; and 4+, 1000 mg/dl. Measurements of proteinuria were performed by an observer who had no knowledge of the treatment given.

Figure 3A:
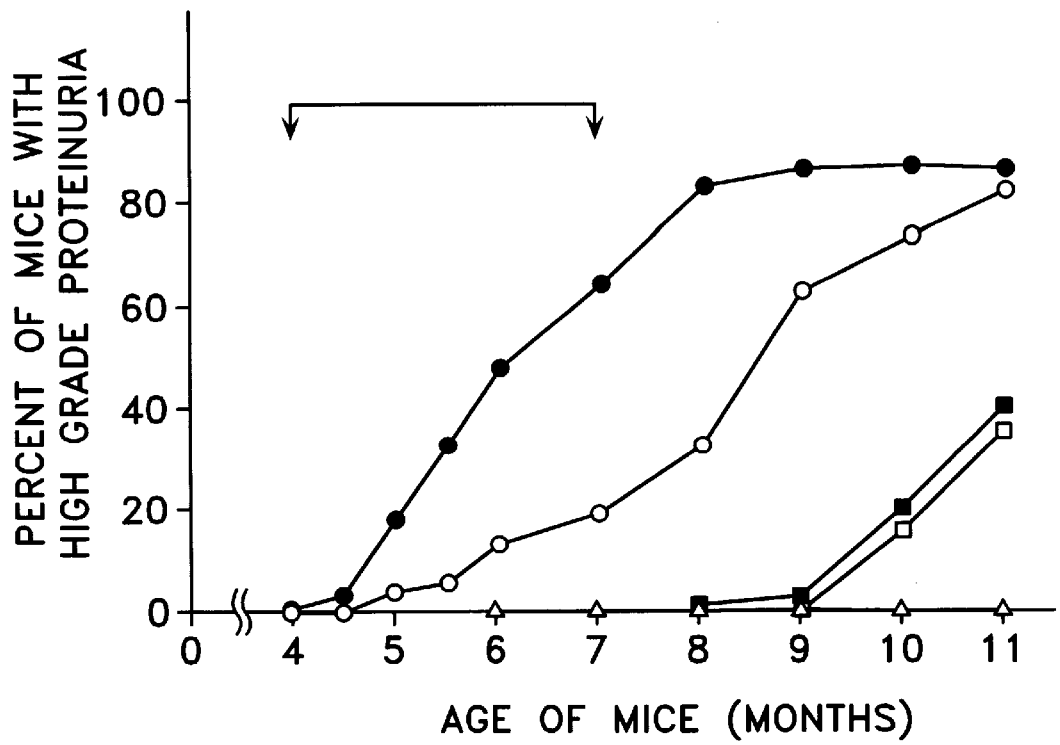
FIG. 3(a) presents a graph showing the cumulative frequency of significant proteinuria in NZB/W $F_1$ mice treated with IFN-γ, compared to treatment with anti-IFN-γ monoclonal antibodies.

FIG. 3(A) shows the cumulative frequency of significant proteinuria resulting after treatment with IFN-γ (closed circles), PBS or nonrelevant monoclonal antibody (open circles), or monoclonal anti-IFN-γ (DB-1) either three times per week (closed squares) or once per week (open squares). There were no significant differences found between PBS versus nonrelevant antibody-treated animals; therefore, they are presented together as a single control group. In order to reflect more accurately the development of renal disease in all mice (alive and dead), a correction factor was introduced. Thus, each point reflects the current level of proteinuria as well as the last measurement of proteinuria in deceased mice. Arrows indicate the time period of the different treatments.

As seen in FIG. 3(A), the development of high grade proteinuria was significantly delayed by treatment of the mice with DB-1 and stimulated by treatment with IFN-γ. At 8 months the development of high grade proteinuria was not detected in the DB-1 mice, while approximately 30% of the control mice and approximately 80% of the IFN-γ treated mice had high-grade proteinuria. In addition, the onset of high-grade proteinuria was delayed five months by the DB-1 treatment. In fact, the onset of high-grade proteinuria was not detected until 3 months after the treatment with DB-1 had ceased, raising the possibility that continued treatment with DB-1 may have further prevented the development of high-grade proteinuria.

The delaying effect of DB-1 on high-grade proteinuria parallels its dramatic effect on survival, as shown supra.

I.B.3. Effect on the Appearance of Anti-DNA Antibodies

The presence of anti-DNA specific antibodies in NZB/W $F_1$ mice were determined by using a modification of a linked immunosorbent assay (ELISA) described by Zouali and Stollar (1986), J. Immunol. Methods 90, 105. More specifically, polystyrene microtiter plates were irradiated with UV germicidal lamps for 12 hours followed by incubation with 100 μl of nucleic acid solution (10 μ/ml) in PBS, for 2 hours at room temperature (RT). Serum samples were incubated for 1 hr at RT. Bound antibodies were revealed with peroxidase-conjugated goat anti-mouse IgG (Tago, Inc., Burlingame, Calif.). Absorbance at 405 nm was read with a multiscan automatic spectrophotometer (Dynatech).

Figure 3B:
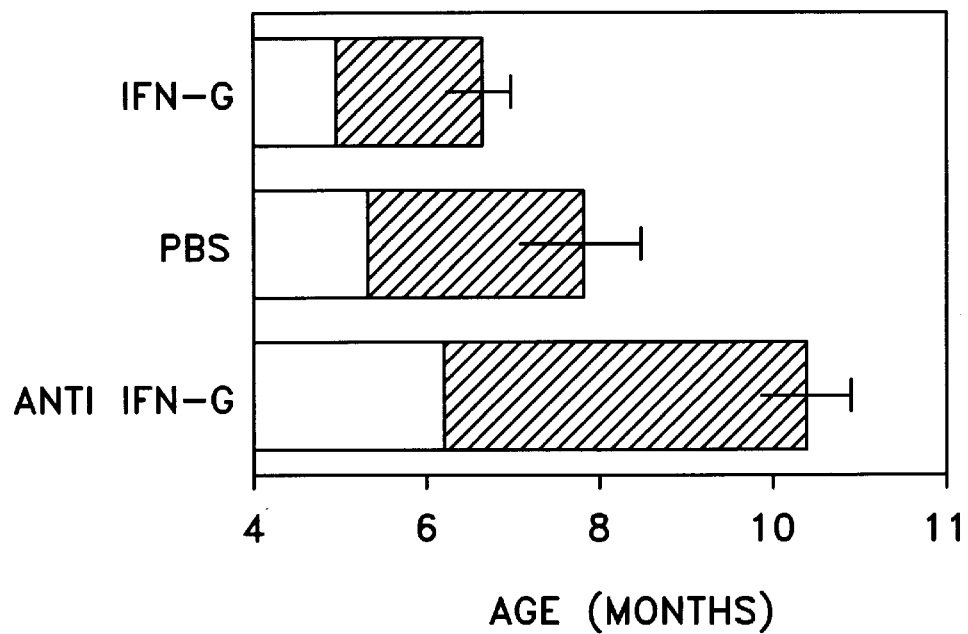
FIG. 3(b) presents a bar graph showing the effect of various treatments on the appearance of anti-DNA antibodies.

FIG. 3(B) shows the effect of treatment with DB-1 and with IFN-γ, as compared to controls, on the appearance of anti-DNA antibodies. The open bars represent the mean age at which anti-DNA antibodies were detected in the various groups, while dashed bars represent the mean age at which peak levels of anti-DNA antibody occurred. Note: at the age when anti-DNA antibody was detected, the difference between the PBS and IFN-γ-treated groups is not significant, while the difference between PBS and DB-1 treated groups is significant (p 0.05). The differences in age at peak levels between PBS-treated versus IFN-γ or DB-1-treated groups are significant (p 0.005 and p 0.0005, respectively).

As shown in FIG. 3(B), treatment with DB-1 delayed both the age at which anti-DNA antibodies were first detected and the age at which maximum levels of anti-DNA antibodies appeared. In both the IFN-γ-treated and the control mice, anti-DNA antibodies were first detected at about 5 months of age, as compared to between 6 and 7 months for the DB-1-treated mice. Maximum levels of DNA antibodies were seen at approximately 11 months in the DB-1-treated mice, whereas the appearance of maximum levels was at approximately 7 months and 8 months for the IFN-γ-treated and control mice, respectively.

II. Treatment of SJL/J Female Mice Immunized with Acetyl Choline Receptor Protein (AcChoR), with Anti-IFN-γ Antibodies: A Model System for Myasthenia Gravis in Humans Myasthenia gravis is one of several human autoimmune diseases linked to HLA-D. Safenberg et al. (1978), Tissue Antigens 12, 136; McDevitt and Engelman (1977) Arth. Rheum. 20, 59. In myasthenia gravis, antibodies to the acetyl choline receptors (AcChoR) impair neuromuscular transmission by mediating loss of AcChoR in the postsynaptic membrane. Kao and Drachman (1977), Science 196, 527; Heinemann et al. (1977), Proc. Natl. Acad. Sci. U.S.A. 74, 3090.

SJL/J female mice are a model system for human myasthenia gravis. Waldor et al. (1983) 80, 2713. In these animals, experimental autoimmune myasthenia gravis (EAMG) is induced by immunizing the mice with soluble AcChoR protein from another species. Susceptibility to EAMG is linked in part to the MHC and has been mapped to the I region within H-2. Christadoss et al. (1979), J. Immunol. 123, 2540.

II.A. Methods of Inducing Antibodies to AcChoR and of Inducing Clinical EAMG AcChoR protein is purified from *Torpedo californica* and assayed according to the method of Waldor et al. (1983). Proc. Natl. Acad. Sci. U.S.A., 2713, which is hereby incorporated by reference.

EAMG is induced in SJL/J mice by immunization with AcChoR. More specifically, emulsified AcChoR, 15 μg in complete Freund adjuvant is injected intradermally among six sites on the back, the hind foot pads, and the base of the tail. Animals are reimmunized with this same regimen 4 weeks later.

II.B. Treatment of AcChoR Immunized SJL/J mice with Anti-IFN-γ Antibodies

Treatment of the mice is as follows. Animals are divided into three matched groups. Treatment with anti-IFN-γ antibody is as follows: group 1 is treated prior to the initial immunization with AcChoR, group 2 is treated between the first and second immunization, and group 3 is treated immediately after the second immunization. Control groups of animals are treated according to this schedule, substituting PBS or irrelevant monoclonal antibody for anti-IFN-γ antibody.

II.B.1. Effect of the Treatment on the Titer of Anti-AcChoR Antibodies

Anti-AcChoR antibody levels are measured by a microtiter ELISA assay as described in Waldor et al., supra. More specifically, The standard reagent volume is 50 μl per well. Reagents are usually incubated in the wells for 2 hr at RT. Five Vg of AcChoR diluted in bicarbonate buffer, pH 9.6, is added to each well. After incubation with AcChoR, the plates are rinsed four times with a wash solution consisting of phosphate-buffered saline containing 0.05% Tween and 0.05% $NaN_3$. Mouse sera are diluted in 0.01M PBS (pH 7.2), 1.5 mM $MgCl_2$, 2.0 mM 2-mercaptoethanol, 0.05% Tween-80, 0.05% $NaN_3$ (P-Tween buffer) and incubated on the plate. After the plate is washed, β-galactosidase-conjugated sheep anti-mouse antibody diluted in P-Tween buffer is added to each well. After a final washing, the enzyme substrate, p-nitrophenyl-galactopyranoside is added to the plate, and the degree of substrate catalysis is determined from the absorbance at 405 nm after 1hr.

Anti-AcChoR antibodies are expected to be present in the immunized untreated mice as compared to nonimmunized mice. Treatment with anti-IFN-γ is expected to significantly reduce the titer of anti-AcChoR antibodies. Mice treated with PBS and with an irrelevant monoclonal antibody are expected to have titers equal to that in immunized untreated mice.

II.B.2. Effect on Clinical EAMG

The effect of treatment with anti-IFN-γ on clinical EAMG is assessed. Myasthenia symptoms include a characteristic hunched posture with drooping of the head and neck, exaggerated arching of the back, splayed limbs, abnormal walking, and difficulty in righting. Mild symptoms are present after a standard stress test involving swimming. Berman and Patrick (1980), J. Exp. Med. 151, 204. Weakness is ameliorated (unless the mice are moribund) within 5–10 minutes of administration of neostigmine bromide (0.0375 mg/kg) and atropine sulfate (0.015 mg/kg) intraperitoneally.

Treatment of AcChoR-immunized mice with anti-IFN-γ antibody is expected to prevent or ameliorate the clinical symptoms of EAMG.

III. Treatment of Mice with Collagen-Induced Arthritis with Anti-IFN-γ Antibodies: A Model for Human Rheumatoid Arthritis In humans, susceptibility to rheumatoid arthritis is associated with HLA D/DR. Thomson, supra. The immune response in mice to native type II collagen has been used to establish an experimental model of arthritis with a number of histological and pathological features resembling human rheumatoid arthritis. Susceptibility to collagen-induced arthritis (CIA) in mice has been mapped to the H-2 I region, particularly the I-A subregion. Huse et al. (1984), Fed. Proc. 43, 1820.

Mice from a susceptible strain, DBA-1, are caused to have CIA by treatment of the mice with native type II collagen, using the technique described in Wooley and Luthra (1985). J. Immunol. 134, 2366, which is hereby incorporated herein by reference.

The mice are treated with anti-IFN-γ antibodies as follows: group 1 is treated one day prior to immunization with type II collagen, group 2 is treated one day after immunization, and group 3 is treated 2 days after immunization. Control groups of animals are treated according to this schedule, substituting PBS or irrelevant monoclonal antibodies for anti-IFN-γ antibodies.

The effect of anti-IFN-γ antibody treatment on manifestations of the disease are monitored. These manifestations include antibody titers to collagen, histologic changes, and clinical symptoms associated with the disease.

Treatment with anti-IFN-γ antibody is expected to cause a lessening of the antibody titer to collagen, relative to that in immunized untreated mice or immunized control mice. It also is expected to cause a lessening in the histological changes and an amelioration or prevention of the clinical symptoms.

IV. Treatment of BB Rats with Anti-IFN-γ Antibodies: A Model System for Insulin-Dependent Diabetes Mellitus (IDDM) and for Thyroiditis in Humans IDDM is observed as a consequence of the selective destruction of insulin-secreting cells within the islets of Langerhans of the pancreas. Involvement of the immune system in this disease is suggested by morphologic evidence of early infiltration of the islets by mononuclear cells, by the detection of anti-islet cell antibodies, by the high frequency of HLA-DR3 and -DR4 alleles in IDDM populations, and by clinical associations between IDDM and various autoimmune diseases. An animal model for spontaneous IDDM and thyroiditis has been developed in the BB rat. As in humans, the rat disease is controlled in part by the genes encoding the MHC antigens. is characterized by islet infiltration, and is associated with the presence of anti-islet antibodies. The I-E equivalent class II MHC antigens appear to be involved in manifestation of the autoimmune diseases in the BB rat. Boitard et al. (1985), Proc. Natl. Acad. Sci. U.S.A. 82, 6627.

The rats are treated with anti-IFN-γ antibodies as follows. A first group receives weekly intraperitoneal injections of anti-IFN-γ antibody beginning at an early age, well before clinical symptoms of diabetes are manifest, i.e., at about 35 days old. A second group is treated similarly, but treatment is begun at a later age, i.e., at about 70 days old; nevertheless, treatment is still begun before the full manifestation of clinical diabetes. For these purposes, clinical diabetes is determined by urine glucose levels. Control groups of animals are treated according to this schedule, substituting PBS or irrelevant monoclonal antibody for anti-IFN-γ antibody.

Prior to the first injection, each animal is starved overnight and checked for normoglycemia. Animals are clinically evaluated every other day for body weight and glycosuria. Glycosuric animals are bled for a plasma sample for glucose determination. Diabetic animals have a 4-hr fasting glycemia value of >16 mmol/liter. All diabetic animals are sacrificed when ketotic for collecting a blood sample for serum and pancreas and thyroid tissue samples for morphological evaluation. All nondiabetic animals are sacrificed at age 120 days for collecting an overnight fasting plasma sample for glucose determination, a blood sample for serum, and pancreas and thyroid tissue for morphologic evaluation.

In morphologic evaluation, insulitis is characterized by the presence of mononuclear inflammatory cells within the islets. Thyroiditis is characterized by focal interstitial lymphocytic infiltrate within the thyroid gland, as a minimum criterion. Most severe cases show diffuse extensive lymphocytic infiltrates, disruption of acini, fibrosis, and focal Hurthle cell change. See Boitard et al., supra.

Treatment of the BB rats with anti-IFN-γ antibodies is expected to ameliorate or prevent the manifestation of the clinical and morphological symptoms associated with IDDM and thyroiditis.

V. Treatment of Non-Obese Diabetic (NOD) Mice with Anti-IFN-γ Antibodies: A Model for Human IDDM The NOD mouse strain (H-2$K^d D^b$) is a murine model for autoimmune IDDM. The disease in these animals is characterized by anti-islet cell antibodies, severe insulitis, and evidence for autoimmune destruction of the β-cells. Makino et al. (1980), Exp. Anim. 29: Kanazawa et al. (1984), Diabetologia 27, 113. The disease can be passively transferred with lymphocytes and prevented by treatment with cyclosporin-A. Ikehara et al. (1985), Proc. Natl. Acad. Sci. U.S.A. 82, 7743; Mori et al. (1986), Diabetologia 29, 244. Untreated animals develop profound glucose intolerance and ketosis and succumb within weeks of the onset of the disease. seventy to ninety percent of female and 20–30% of male animals develop diabetes within the first six months of life. Breeding studies have defined at least two genetic loci responsible for disease susceptibility, one of which maps to the MHC. Characterization of NOD Class II antigens at both the serologic and molecular level suggest that the susceptibility to autoimmune disease is linked to I-$A_\beta$. Acha-Orbea and McDevitt (1987), Proc. Natl. Acad. Sci. U.S.A. 84, 235.

Female NOD mice are treated with anti-IFN-γ antibodies as follows. A first group receives weekly intraperitoneal injections of anti-IFN-γ antibody beginning within 24 hours after birth. A second group is treated similarly, but treatment is begun when the mice are adult, i.e., the first injection is 2 weeks after birth. Control groups of animals are treated according to this schedule, substituting PBS or irrelevant monoclonal antibody for anti-IFN-γ antibody. After 3 months the animals are monitored for urine levels of glucose to measure disease onset.

Treatment of Female NOD mice with anti-IFN-γ-antibodies is expected to lengthen the time before the onset of diabetes and/or to ameliorate or prevent the disease.

While the present invention has been illustrated above by certain specific embodiments, it is not intended that these specific examples limit the scope of the invention as described in the appended claims.

VI. Treatment of Rats with Adjuvant-Induced Arthritis with Anti-IFN-γ Antibodies: A Model for Human Rheumatoid Arthritis Adjuvant arthritis in rats is an experimental model for human arthritis, and a prototype of autoimmune arthritis triggered by bacterial antigens. Holoshitz et al (1986) in Prospects of Immunology (CRC Press); Pearson (1964), Arthritis Rheum. 7, 80. The disease is the result of a cell-mediated immune response, as evidenced by its transmissiblity by a clone of T-cells which were reactive against the adjuvant (MT); the target self-antigen in the disease, based upon studies with the same cloned cells, appears to be part(s) of a proteoglycan molecule of cartilage. Holoshitz et al, supra.

Adjuvant disease in rats is produced as described by Pearson, supra., i.e., by a single injection of Freund's adjuvant (killed tubercle bacilli or chemical fractions of it, mineral oil, and an emulsifying agent) given into several depot sites, preferably intracutaneously or into a paw or the base of the tail. The adjuvant is given in the absence of other antigens.

The rats are treated with anti-IFN-γ antibodies as follows: group 1 is treated one day prior to injection of adjuvant, group 2 is treated one day after immunization, and group 3 is treated 2 days after immunization. Control groups of animals are treated according to this schedule, substituting PBS or irrelevant monoclonal antibodies for anti-IFN-γ antibodies.

The effect of anti-IFN-γ antibody treatment on manifestations of the disease are monitored. These manifestations are histopathological, and include an acute and subacute synovitis with proliferation of synovial lining cells, predominantly a mononuclear infiltration of the articular and particular tissues, the invasion of bone and articular cartilage by connective tissue pannus, and periosteal new bone formation, especially adjacent to affected joints. In severe or chronic cases, destructive changes occur. as do fibrous or bony ankylosis. These histopathological symptoms are expected to appear in control animals at about 12 days after sensitization to the Freund's adjuvant.

Treatment with anti-IFN-γ antibody is expected to cause an alleviation of the histopathological symptoms associated with adjuvant induced arthritis.

Utility

The various embodiments of the invention are useful for the treatment of individuals susceptible to autoimmune diseases, particularly those linked to or involving the Class II antigens encoded within the MHC. The treatment with anti-IFN-γ antibodies of individuals susceptible to systemic lupus erythematosus who do not yet have full manifestation of the associated nephritis delays the onset of nephritis and ameliorates the clinical symptoms of the disease.

We claim:

1. An immunotherapeutic method for treating an individual afflicted with systemic lupus erythematosus comprising administering to an individual afflicted with systemic lupus erythematosus a disease-controlling amount of at least one antibody which binds to gamma interferon (IFN-gamma) sufficient to limit or reduce at least one clinical manifestation of systemic lupus erythematosus.

2. The method of claim 1 wherein the individual is human.

3. The method of claim 2 wherein the at least one antibody is polyclonal.

4. The method of claim 2 wherein the at least one antibody is monoclonal.

5. The method of claim 1 wherein the administration is parenteral.

6. The method of claim 1 wherein the administration is intravenous.

7. The method of claim 6 wherein the at least one antibody is in a concentration in the range of 1 to 20 mg/ml of a pharmaceutically acceptable parenteral vehicle.

8. The method of claim 1 wherein the amount of the at least one antibody is in the range of 0.1 to 2.0 grams per liter of blood volume of the individual.

9. The method of claim 1, wherein the at least one clinical manifestation is selected from the group consisting of proteinuria, mortality, and elevated levels of anti-DNA antibodies.

* * * * *

UNITED STATES PATENT AND TRADEMARK OFFICE
CERTIFICATE OF CORRECTION

PATENT NO. : 6,036,956
DATED : March 14, 2000
INVENTOR(S) : Chaim O. JACOB, et al.

It is certified that error appears in the above-identified patent and that said Letters Patent is hereby corrected as shown below:

At Page 1, section [54], please delete the title "METHOD AND DOSAGE FORM USING AN ANTAGONIST TO GAMMA INTERFERON TO CONTROL MHC-ASSOCIATED AUTOIMMUNE DISEASE" and replace with amended title "METHOD OF TREATMENT FOR SYSTEMIC LUPUS ERYTHEMATOSUS BY ADMINISTERING ANTIBODIES TO GAMMA INTERFERON".

At page 1, section [57], under ABSTRACT, line 3, please replace "administerring" with "administering".

At column 1, line 11, please delete "gamma interferon (IFN-gamma)."

Signed and Sealed this

Fifteenth Day of May, 2001

Attest:

NICHOLAS P. GODICI

Attesting Officer     Acting Director of the United States Patent and Trademark Office